United States Patent [19]

Pilgram

[11] 4,313,755
[45] Feb. 2, 1982

[54] N-CYCLOPYOPYL-N-(FLUOROPHENYL)-N-ACYLUREAS AND THEIR HERBIDICAL USE

[75] Inventor: Kurt H. Pilgram, Modesto, Calif.

[73] Assignee: Shell Oil Company, Houston, Tex.

[21] Appl. No.: 230,777

[22] Filed: Feb. 2, 1981

Related U.S. Application Data

[63] Continuation-in-part of Ser. No. 170,421, Jul. 21, 1980, abandoned.

[51] Int. Cl.$^3$ .................... E05B 63/14; C07C 127/22
[52] U.S. Cl. ........................................ 71/120; 71/118; 564/45
[58] Field of Search ..................... 71/120; 564/45

[56] References Cited

U.S. PATENT DOCUMENTS

| | | | |
|---|---|---|---|
| 2,762,695 | 9/1956 | Gerjovich et al. | 564/45 X |
| 2,762,696 | 9/1956 | Gerjovich et al. | 564/45 X |
| 3,469,965 | 9/1969 | Bruce et al. | 71/68 |
| 3,518,304 | 6/1970 | Swithenbank et al. | 260/553 |
| 3,705,028 | 12/1972 | Janiak et al. | 564/45 X |
| 3,734,961 | 5/1973 | Englehart | 564/54 |
| 3,946,062 | 3/1976 | Cleveland | 71/98 |

FOREIGN PATENT DOCUMENTS

| | | | |
|---|---|---|---|
| 668792 | 12/1965 | Belgium | 71/118 |
| 849570 | 6/1970 | Belgium | 71/120 |
| 1330667 | 9/1973 | United Kingdom | 564/45 |
| 1341153 | 12/1973 | United Kingdom | 564/45 |
| 1410493 | 10/1975 | United Kingdom | 564/45 |

*Primary Examiner*—John Doll

[57] ABSTRACT

Certain N'-cyclopropyl-N-(fluorophenyl)-N-acylureas, useful as selective herbicides.

3 Claims, No Drawings

N-CYCLOPYOPYL-N-(FLUOROPHENYL)-N-ACYLUREAS AND THEIR HERBIDICAL USE

This application is a continuation-in-part of application Serial No. 170,421 filed July 21, 1980 now abandoned.

DESCRIPTION OF THE INVENTION

It has been found that N'-cyclopropyl-N-(fluorophenyl)-N-acylureas, described by the formula

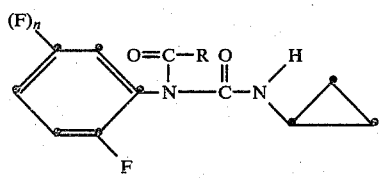

wherein n is zero or one, and R is hydrogen or methyl, effectively control weeds in grain sorghum plantings without significant injury to the sorghum plants.

The compounds of the invention have been prepared as described in the following examples. In each case, the identities of the product and any intermediate involved were confirmed by appropriate chemical and spectral analyses.

EXAMPLE 1

N'-cyclopropyl-N-(2-fluorophenyl)-N-formylurea (1)

A mixture of 600 ml of ortho-dichlorobenzene, 103.9 g of sodium azide and 151 g of cyclopropanecarboxylic acid chloride was heated under a nitrogen atmosphere at 110°–130° for 6 hours. The mixture was distilled and the distillate was redistilled to give cyclopropyl isocyanate, (1A), as a liquid, b.p.: 93°–98° C. (1 Torr.).

A mixture of 25 g of 2-fluoronitrobenzene, 250 ml of tetrahydrofuran and 0.5 of a commercial palladium catalyst (5% on charcoal) was hydrogenated (50 psig hydrogen pressure) in a Parr shaker at room temperature. A mixture of the 2-fluoroaniline thus formed and a ten percent molar excess of formic acid in toluene was refluxed for 2 hours, water of reaction being removed as formed. The resulting mixture was distilled to 90°–95° C., 0.05 Torr. On cooling, the product crystallized to give N-(2-fluorophenyl)formamide (1B), as a solid, m.p.: 47°–48° C.

An equimolar mixture of 1A and 1B in tetrohydrofuran was stirred for 2 days at 100° C. The solvent was evaporated, and the residue was recrystallized from ether to give 1, as a white solid, m.p.: 104°–105° C.

EXAMPLE 2

N'-cyclopropyl-N-(2,5-difluorophenyl)-N-formylurea (2)

A solution of 2,5-difluoronitrobenzene in tetrahydrofuran containing Raney nickel catalyst, in a Parr shaker, was treated with hydrogen at room temperature to give 2,5-difluoroaniline (2A).

A mixture of 25.8 g of 2A, 18.5 g of formic acid and 100 ml of benzene was refluxed (80° C.) for 2 hours. The mixture was allowed to stand overnight. The solid that formed was separated and taken up in ether. Hexane was added. The solid that formed was separated and washed with cold hexane to give N-(2,5-difluorophenyl)formamide (2B), m.p.: 112°–114° C.

A mixture of 9.9 g of 2B, 25 ml of dimethylformamide, 11 g of 1A and 2 g of triethylamine (catalyst) was heated in a steam bath for 24 hours. The resulting mixture was diluted with ether and water, and phase-separated. The ether phase was washed with water, and dried (MgSO$_4$), and the solvent was evaporated. The residue was triturated with ether. The residual off-white solid was 2, m.p.: 118°–120° C.

EXAMPLE 3

N'-cyclopropyl-N-(2-fluorophenyl)-N-acetylurea (3)

25 ml of acetic anhydride was added to a mixture of 11.1 g of 2-fluoroaniline and 25 ml of glacial acetic acid. The mixture was heated at reflux for 5 minutes, then diluted with ice water. The resulting mixture was filtered, and the solid was dried to give N-(2-fluorophenyl)acetamide (3A), as a white solid, m.p.: 76°–77° C.

A mixture of 5.8 g of 3A, 50 ml of tetrahydrofuran and 5.0 g of 1A was heated in a sealed glass cylinder for 12 hours at 100° C. Then the solvent was evaporated, and the residue was recrystallized from ether/hexane to give 3, as a white solid, m.p.: 43°–45° C.

Compounds of the invention have been found to be useful for inhibiting growth of unwanted plants, giving control of both broad-leaved plants and grasses. They appear to be more effective when applied preemergence (applied to the soil before the seeds have sprouted), than when applied postemergence (applied to the foliage of the growing plants).

At the dosages that have given effective control of unwanted plants, the compounds of the invention have not caused significant injury to grain sorghum plants.

It has been found that the compounds of the invention tend to hydrolyze when in contact with moisture, particularly when the pH of the mixture is above 7.0. This instability of the compounds of the invention must be taken into account when handling, formulating and storing them.

For application to the locus to be treated, the compound of the invention preferably is formulated with a carrier, or a surface-active material, or both.

By "carrier" is meant a solid or a fluid material, which may be inorganic or organic and of synthetic or natural origin, with which the urea is mixed or formulated to facilitate its application to the plant, seed, soil or other object to be treated, or its storage, transport or handling.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonates; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols; bitumen, waxes such as, for example, beeswax, paraffin wax, and chlorinated mineral waxes; and solid fertilizers, for example, superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquified normally vaporous gaseous compounds. Mixtures of different liquids are often suitable. The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols and alkyl-phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions may be formulated as wettable powders, dusts, granules, solutions, emulsifiable concentrates, emulsions, suspension concentrates and aerosols. Wettable powders are usually compounded to contain 25, 50 and 75% by weight of toxicant and usually contain in addition to solid carrier, 3–10% by weight of a dispersing agent, 15% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing ½–10% by weight of toxicant. Granules are usually prepared to have a size between 10 and 100 BS mesh (1.676–0.152 mm), and may be manufactured by agglomeration or impregnation techniques. Generally, granules will contain ½–25% by weight toxicant and 0–1% by weight of additives such as stabilizers, slow release modifiers and binding agents. Emulsifiable concentrates usually contain, in addition to the solvent and, when necessary, cosolvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight toxicant, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water. Aqueous dispersions and emulsions, for example, compositions obtained by diluting a wettable powder or a concentrate with water, also are suitable. The said emulsions may be of the water-in-oil or of the oil-in-water type, and may have a thick mayonnaise-like consistency.

The compositions may also contain other ingredients, for example other compounds possessing pesticidal, especially insecticidal, acaricidal, herbicidal or fungicidal properties.

Protection of a locus or area from undesirable plants is effected by applying the urea, ordinarily in a composition of one of the aforementioned types, to the foliage of the plants or plant growth medium, e.g., soil in which the plant is growing or in which the seeds are present. The urea, of course, is applied in amounts sufficient to exert the desired action.

The amount of the urea to be used in controlling undesirable vegetation will naturally depend on the condition of the vegetation, the degree of activity desired, the formulation used, the mode of application, the climate, the season of the year, and other variables. Recommendations as to precise amounts are, therefore, not possible. In general, however, application to the locus to be protected of from 0.1 to 10.0 kilograms per hectare of the area will be satisfactory.

EXAMPLES OF HERBICIDAL ACTIVITY

In the following examples, the species of plants that were tested were:
Barnyardgrass (watergrass)—*Echinochloa crus-galli*
Large crabgrass—*Digitaria sanguinalis*
Downy brome—*Bromus tectorum*
Giant foxtail—*Setaria faberii*
Wild oats—*Avena fatua*
Yellow foxtail—*Setaria lutescens*
Hemp sesbania—*Sesbania exaltata*
Jimsonweed—*Datura stramonium*
Ivyleaf morningglory—*Ipomea hederacea*
Wild mustard—*Brassica kaber*
Redroot pigweed—*Amaranthus retroflexus*
Prickly sida—*Sida spinosa*
Sicklepod—*Cassia obtusifolia*
Velvetleaf—*Abutilon theophrasti*
Garden cress—*Lepidium sativum*
Grain sorghum—*Sorghum vulgare* (Pioneer 265)
Corn—*Zea maize* (deKalb X363)
Cotton—*Gossypium hirsutum* (Acala SJ-2)
Rice—*Oryza sativa* (Calrose)
Soybean—*Glycine max* (Amsoy 71)
Wheat—*Triticum aestivum* (Cajeme 71)
Sugar beet—*Beta vulgaris*
Cocklebur—*Xanthum pennsylvanicum*
Johnsongrass—*Sorghum halepense*

EXAMPLE 1

The preemergence herbicidal activity provided by Compounds 1, 2 and 3 was evaluated by planting seeds of barnyardgrass, garden cress, downy brome, velvetleaf, yellow foxtail, and sicklepod in test tubes, nominally measuring 25×200 millimeters, filled about three-quarters full of untreated soil, in each case covered on top with about 2.5 cubic centimeters of soil treated with the test compound at the rates of 0.1 and 1 milligram respectively, Table I at Rates I and II, respectively. The dosages were approximately two and twenty pounds of test compound per acre, respectively. The seeds were planted in the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
| --- | --- |
| 9 | No living tissue |
| 8 | Living tissue, but plant expected to die |
| 7 | Plant badly damaged, but expected to live |
| 6 | Plant badly damaged, but expected to recover completely |
| 5 | Unacceptable damage for crop plants, insufficient damage to weeds |
| 3-4 | Definite damage |
| 1-2 | Plant slightly affected, possibly by the chemical, possibly due to biological variability |
| 0 | No visible effect |

The postemergence activity provided by Compounds 1, 2 and 3 was evaluated by spraying 10-day old large crabgrass plants, 13-day old redroot pigweed plants, 6-day old downy brome plants, 9-day old velvetleaf plants, 9-day old yellow foxtail plants and 9-day old sicklepod plants to runoff with a liquid formulation of the test compound at the rates of 2.4 milliliters of a 0.025% solution (about one pound of the test compound per acre), designated Rate I in table I, and 2.4 milliliters of a 0.25% solution (about ten pounds of the test compound per acre), designated Rate II in Table I. The sprayed plants were held under controlled conditions of temperature, moisture and light for 7 to 8 days and the effect of the test compound was then evaluated visually, the results being rated on the 0 to 9 scale described above.

The results of the tests are summarized in Table I.

pound on the soil in which seeds of the test plants had been sown. In each series of tests, the plants were grown in narrow trays and sprayed with the test compound. The solution of the test compound was sprayed over the tray, from one end to the other, the concentration of the test compound in the formulation varying logarithmically from a higher value (5 pounds of the test compound per acre) at one end of the band to a lower value (0.55 pound of the test compound per acre) at the other end of the band. The effect of the test compound was evaluated visually and reported as the nominal rate of application, in pounds of the test compound per acre of soil band, at which 90% inhibition of the growth of the plants occurred this being referred to as the 90% growth inhibition, or $GID_{90}$, dosage. Results of the test, as well as the plant species involved, are set out in Table II.

TABLE II

| | $GID_{90}$ | | | | | | |
| --- | --- | --- | --- | --- | --- | --- | --- |
| Compound | Barn-yard-grass | Downy Brome | Yellow Foxtail | Crab-grass | Velvet-leaf | Johnson-grass | Grain Sorghum |
| 1 | 1.0 | −0.55[a] | −0.55 | 0.7 | −0.55 | 1.3 | 2.1 |
| 2 | 0.55 | 0.10 | 0.15 | 0.16 | −0.055 | 0.45 | 2.3 |
| 3 | 5.0 | 1.9 | 4.1 | 0.8 | −0.055 | 2.5 | +5.0 |

[a] "−" indicates "less than"; [b] "+" indicates "more than".

EXAMPLE 3

The postemergence herbicidal activity provided by Compounds 1 and 2 was further determined with respect to several common species of weeds, and grain sorghum, by spraying a formulation of the test compound on the foliage of young growing plants. In each series of tests, the plants were grown in narrow trays and sprayed with the formulation. The formulation of the test compound was sprayed over the tray, from one end to the other, the concentration of the test compound in the formulation varying logarithmically from a higher value (5 pounds per acre) at one end of the series to a lower value (0.55 pound acre) at the other end of the series. The effect of the test compound was evaluated visually and reported as the nominal rate of

TABLE I

| | | Preemergence (Soil) | | | | | | | | | | | Postemergence (Foliar) | | | | | | | | | |
| --- | --- | --- | --- | --- | --- | --- | --- | --- | --- | --- | --- | --- | --- | --- | --- | --- | --- | --- | --- | --- | --- | --- |
| | | Barn-yard-grass | | Garden Cress | | Downy Brome | | Velvet-leaf | | Yellow Foxtail | | Sickle-pod | | Crab-grass | | Pig-weed | | John-son-grass | | Velvet-leaf | | Yellow Foxtail | | Sickle-pod |
| Compound | Dosage | I | II | I | II | I | II | I | II | I | II | I | II | I | II | I | II | I | II | I | II | I | II | I | II |
| 1 | | 9 | 9 | 9 | 9 | 9 | 9 | 9 | 9 | 9 | 9 | 9 | 9 | 5 | 6 | 7 | 9 | 3 | 6 | 7 | 9 | 5 | 9 | 7 | 9 |
| 2 | | 9 | 9 | 9 | 9 | 8 | 9 | 9 | 9 | 9 | 9 | 9 | 9 | 5 | 7 | 7 | 9 | 4 | 9 | 8 | 9 | 9 | 9 | 9 | 9 |
| 3 | | 9 | 9 | 9 | 9 | 6 | 8 | 9 | 9 | 8 | 9 | 9 | 9 | 1 | 1 | 8 | 8 | 2 | 4 | 8 | 9 | 6 | 8 | 8 | 9 |

EXAMPLE 2

The preemergence herbicidal activity provided by Compounds 1, 2 and 3 was further determined with respect to several common species of weeds, and grain sorghum, by spraying a formulation of the test comapplication, in pounds of the test compound applied per acre, at which 90% inhibition of the growth of the plants occurred, this being referred to as the 90% growth inhibition or $GID_{90}$ dosage. Results of the test, as well as the plant species involved, are set out in Table III.

TABLE III

| | $GID_{90}$ | | | | | | |
| --- | --- | --- | --- | --- | --- | --- | --- |
| Compound | Barn-yard-grass | Downy Brome | Yellow Foxtail | Crab-grass | Velvet-leaf | Johnson grass | Grain Sorghum |
| 1 | +5.0 | +5.0 | 3.1 | 1.0 | 0.55 | +5.0 | +5.0 |

TABLE III-continued

| Compound | Barnyardgrass | Downy Brome | Yellow Foxtail | Crabgrass | Velvetleaf | Johnson grass | Grain Sorghum |
|---|---|---|---|---|---|---|---|
| 2 | 3.4 | +5.0 | −0.55 | −0.55 | −0.55 | 2.3 | +5.0 |

[a] "−" indicates "less than"; [b] "+" indicates "more than".

EXAMPLE 4

The preemergence activity provided by Compound 1 was further determined with respect to a number of crop plants and common species of weeds, using the procedure described in Examples 2 and 3, except that the test compound was applied at three different fixed dosages of the compound per acre, and the results were evaluated with reference to the 0–9 scale described in Example 1. The results of the test are reported in Table IV.

Table V reports the results of similar tests with respect to both the preemergence and postemergence activity of Compound 2.

TABLE IV

| | Compound 1 | | |
|---|---|---|---|
| | Rating of Effect at Indicated Dosage (lb/acre) | | |
| | Preemergence | | |
| Plant Species | 0.5 | 1.0 | 2.0 |
| Corn | 5 | 6 | 6 |
| Cotton | 9 | 9 | 9 |
| Rice | 5 | 9 | 6 |
| Grain Sorghum | 0 | 4 | 9 |
| Soybean | 9 | 9 | 9 |
| Sugar beet | 9 | 9 | 9 |
| Wheat | 8 | 8 | 9 |
| Barnyardgrass | 9 | 9 | 9 |
| Crabgrass | 9 | 9 | 9 |
| Downy Brome | 9 | 9 | 9 |
| Giant Foxtail | 5 | 9 | 9 |
| Johnsongrass | 5 | 7 | 9 |
| Wild Oats | 9 | 9 | 9 |
| Yellow Foxtail | 9 | 9 | 9 |
| Cocklebur | 9 | 9 | 9 |
| Hemp sesbania | 9 | 9 | 9 |
| Jimsonweed | 9 | 9 | 9 |
| Morningglory | 9 | 9 | 9 |
| Mustard | 9 | 9 | 9 |
| Pigweed | 9 | 9 | 9 |
| Prickly sida | 9 | 9 | 9 |
| Sicklepod | 9 | 9 | 9 |
| Velvetleaf | 9 | 9 | 9 |

TABLE V

| | Compound 2 | | | | | |
|---|---|---|---|---|---|---|
| | Rating of Effect at Indicated Dosage (lb/acre) | | | | | |
| | Preemergence | | | Postemergence | | |
| Plant Species | 1.0 | 0.5 | 0.25 | 2.0 | 1.0 | 0.5 |
| Corn | 6 | 4 | 3 | 2 | 2 | 0 |
| Cotton | 9 | 9 | 4 | 9 | 9 | 5 |
| Rice | 6 | 6 | 5 | 2 | 2 | 2 |
| Grain Sorghum | 0 | 0 | 2 | 3 | 2 | 2 |
| Soybean | 9 | 9 | 9 | 9 | 9 | 8 |
| Sugar Beet | 9 | 9 | 9 | 9 | 9 | 9 |
| Wheat | 9 | 9 | 9 | 3 | 2 | 1 |
| Barnyardgrass | 9 | 9 | 8 | 3 | 0 | 0 |
| Crabgrass | 9 | 9 | 6 | 8 | 8 | 6 |
| Downy Brome | 9 | 9 | 9 | 3 | 2 | 1 |
| Giant Foxtail | 9 | 9 | 5 | 5 | 5 | 4 |
| Johnsongrass | 9 | 7 | 4 | 5 | 4 | 3 |
| Wild Oats | 9 | 9 | 9 | 9 | 9 | 3 |
| Yellow Foxtail | 9 | 9 | 5 | 8 | 5 | 4 |
| Cocklebur | 9 | 9 | 9 | 8 | 8 | 6 |
| Hemp sesbania | 9 | 9 | 9 | 9 | 9 | 9 |
| Jimsonweed | 9 | 9 | 9 | 9 | 9 | 9 |
| Morningglory | 9 | 9 | 9 | 9 | 9 | 7 |
| Mustard | 9 | 9 | 9 | 9 | 9 | 9 |
| Pigweed | 9 | 9 | 9 | 9 | 9 | 9 |
| Prickly sida | 9 | 9 | 9 | 9 | 9 | 7 |
| Sicklepod | 9 | 9 | 9 | 9 | 9 | 9 |
| Velvetleaf | 9 | 9 | 9 | 9 | 9 | 9 |

I claim:

1. A compound of the formula:

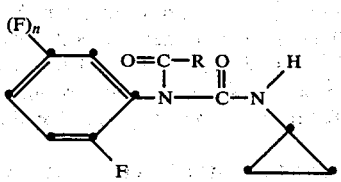

wherein n is zero or one and R is hydrogen or methyl.

2. A herbicidal composition comprising a herbicidally effective amount of a compound of claim 1, together with a carrier, or a surface-active material, or both.

3. A method for controlling weeds in a grain sorghum planting which comprises applying to the locus of the planting an amount of a compound of claim 1 sufficient to control weeds therein.

* * * * *